US006541643B1

(12) United States Patent
Héja et al.

(10) Patent No.: US 6,541,643 B1
(45) Date of Patent: Apr. 1, 2003

(54) PROCESS FOR THE PREPARATION OF SPIRO[CIS-4-(β-HYDROXYETHYLOXY) CYCLOHEXANE-[3H]INDOL]-2'[1'H]ONE DERIVATIVES

(75) Inventors: Gergely Héja, Szentendre (HU); Éva Csikós, Budapest (HU); Csaba Gönczi, Budapest (HU); Judit Halász, Budapest (HU); Félix Hajdú, Budapest (HU); István Hermecz, Budapest (HU); László Kis, Budapest (HU); Lajos Nagy, Szentendre (HU); Andrea Sántáné Csutor, Budapest (HU); Kálmán Simon, Budapest (HU); Tiborné Szomor, Budapest (HU); Györgyné Szvoboda, Dunakeszi (HU)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/030,649

(22) PCT Filed: Jul. 13, 2000

(86) PCT No.: PCT/HU00/00079

§ 371 (c)(1),
(2), (4) Date: Apr. 17, 2002

(87) PCT Pub. No.: WO01/05759

PCT Pub. Date: Jan. 25, 2001

(30) Foreign Application Priority Data

Jul. 15, 1999 (HU) .......................................... P 9902377

(51) Int. Cl.$^7$ ............................................ C07D 209/96
(52) U.S. Cl. ........................................................ 548/411
(58) Field of Search ......................................... 548/411

(56) References Cited

U.S. PATENT DOCUMENTS 5,994,350 A 11/1999 Foulon et al.

FOREIGN PATENT DOCUMENTS

WO WO 97 15556 5/1997

*Primary Examiner*—Joseph K. McKane
*Assistant Examiner*—Sonya Wright
(74) *Attorney, Agent, or Firm*—Michael D. Alexander; Paul E. Dupont

(57) ABSTRACT

The invention relates to a process for the preparation of spiro[cis-4-(β-hydroxyethyloxy)cyclohexane-[3H]indol]-2'[1'H]-one derivatives of the formula (I) wherein $R^1$ and $R^2$ are as defined herein, by reduction of a dispiro[(1,3-dioxolane)-2,4'-cyclohexane-1'3'-[3H]indol]-2"[1"H]-one derivative of general formula (II), wherein $R^1$ and $R^2$ are as defined herein, which comprises carrying out the reduction (a) with sodium cyanoborohydride in the presence of a Lewis acid, or (b) with sodium borohydride in the presence of a strong acid.

7 Claims, 1 Drawing Sheet

I.

II.

PROCESS FOR THE PREPARATION OF SPIRO[CIS-4-(β-HYDROXYETHYLOXY) CYCLOHEXANE-[3H]INDOL]-2'[1'H]ONE DERIVATIVES

This application is a 371 of PCT/HU00/00079 filed Jul. 13, 2000.

The subject of the present invention is a process for the preparation of spiro[cis-4-(β-hydroxyethyloxy) cyclohexane-[3H]indol]-2'[1'H]-one derivatives of general formula I.

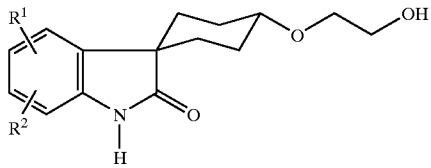

The spiro[cis-4-(β-hydroxyethyloxy)cyclohexane-1,3'-(5'-ethoxy)-[3H]indol]-2'[1'H]-one is an important intermediate to the vasopressin V₂ antagonistic agent, SR 121463. Preparation of. the latter compound and its intermediate of formula I are described in patent application of WO 9715556.

According to the process described in the above patent application, the compounds of general formula I are prepared from the compounds of general formula II

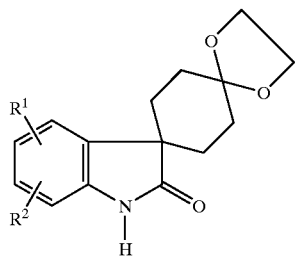

using zinc borohydride reducing agent in the presence of chlorotrimethylsilane in the mixture of dichloromethane and diethyl ether. By this method the desired cis-isomer is obtained in 50–54% yield. The reaction time is long, approximately 20 hours, the zinc borohydride reagent has to be prepared in situ (it also takes approximately 20 hours) and the diethyl ether can not be substituted by an other solvent.

Surprisingly, we have found that the reaction can be accomplished under more simple conditions.

The subject of our invention is a process for the preparation of spiro[cis-4-(β-hydroxyethyloxy)cyclohexane-[3H]indol]-2'[1'H]-one derivatives of the formula I,

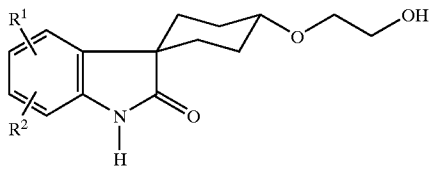

wherein
R¹ and R² stand independently from each other for hydrogen, $C_{1-4}$alkyl, $C_{1-4}$alkoxy, $C_{1-4}$alkylthio, $C_{1-4}$polyfluoroalkyl, $C_{1-4}$polyfluoroalkoxy, $C_{3-7}$cycloalkyloxy, $C_{3-7}$ cycloalkylthio, phenoxy, benzyloxy or nitro group by reduction of a dispiro[(1,3-dioxolane)-2,4'-cyclohexane-1',3''-[3H]indol]-2'' [1''H]-one derivative of the general formula II,

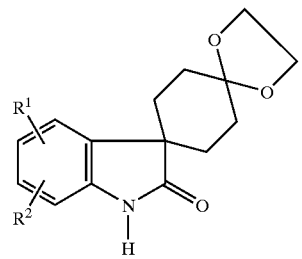

wherein R¹ and R² are as defined above, which comprises carrying out the reduction
a) with sodium cyanoborohydride in the presence of a Lewis acid, or
b) with sodium borohydride in the presence of a strong acid.

Figure 1:
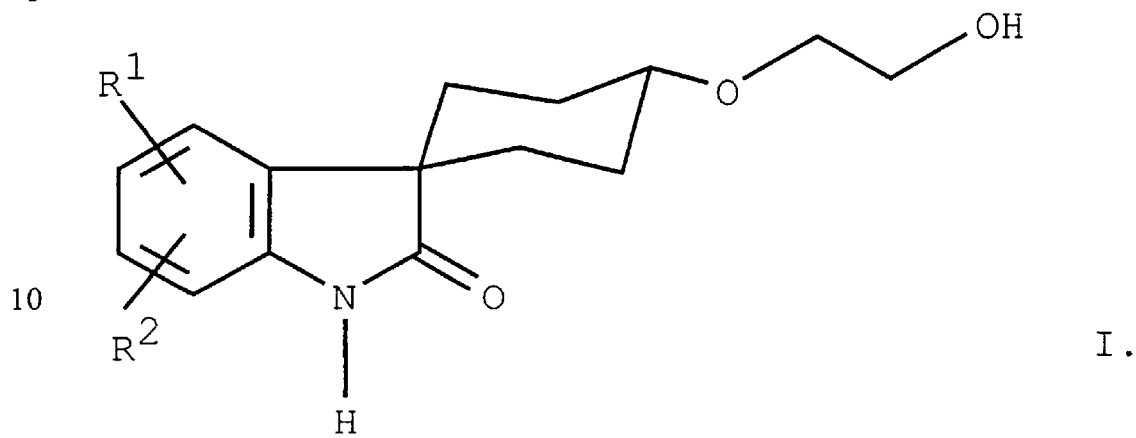
FIG. 1 shows the compounds of formulas I and II.
Figure 1:
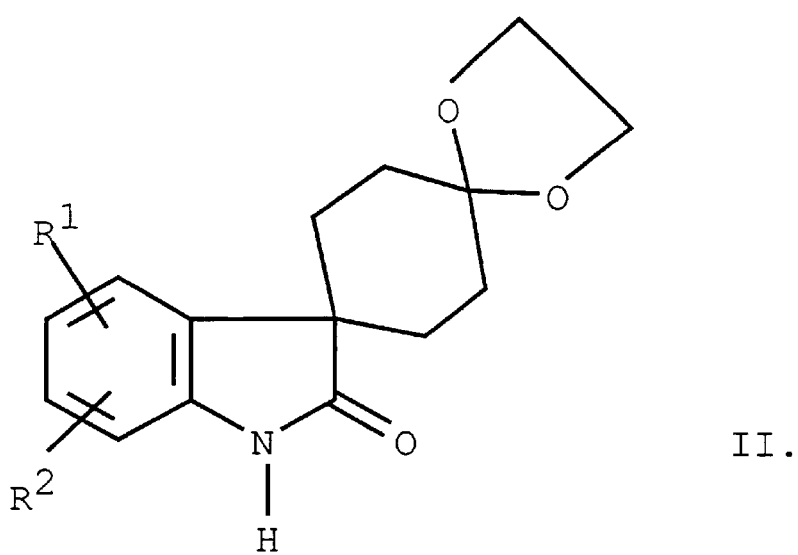

Reducing agents sodium cyanoborohydride and sodium borohydride are available from the market.

In the process according to the present invention as for Lewis acid aluminum chloride, zinc chloride, iron/III/ chloride, preferably boron trifluoride etherate; as for strong organic acid trifluoroacetic acid, dichloro acetic acid, methanesulfonic acid, trifluoromethanesulfonic acid, preferably trichloroacetic acid can be used.

A further advantage of the process of the present invention is that the use of diethyl ether as solvent can be eliminated, as for solvents, halogenated hydrocarbons, preferably dichloromethane can be applied.

By the method according to the present invention the pure cis-isomer can be obtained by 67–75% yield.

Further details of the invention are demonstrated by the following examples, without limiting the claims to the examples.

EXAMPLES

1.) Into the solution made of 121,3 g of dispiro[(1,3-dioxolane)-2,4' cyclohexane-1',3''-(5''-ethoxy)-[3H]indol]-2''[1''H]-one in 1000 ml of dichloromethane, under inert atmosphere 37,2 g of sodium cyanoborohydride is added, then dropwise, at –5° C. 170,3 g of borontrifluoride etherate. The reaction mixture is then allowed to warm up to room temperature (approx. 45 minutes) and stirred at that temperature for 1,5 hours. To the diluted suspension 500 ml of 10% sodium hydroxide solution is dropped and after 30 minutes of stirring dichloromethane is distilled off. After cooling back to room temperature, to the aqueous mixture, slowly, 500 ml of ethanol is added, and the mixture is then stirred and heated at reflux temperature for 1 hour. Ethanol is distilled off in vacuum, the residue is diluted with 300 ml of water, extracted with 4×100 ml of dichloromethane, washed with 2×250 ml of water, dried with sodium sulfate and evaporated. The residual brown oil is dissolved under reflux in 350 ml of toluene, clarified with active carbon and filtered. The precipitating crystals are filtered off. The resulting 100,6 g (82%) product is recrystallized from 300 ml of toluene.

Thus, 91 g product of appropriate purity is obtained. Yield: 74,5%. Ratio of the isomers (HPLC): cis: 95,5%; trans 1,8%.

2.) 9.1 g of dispiro[(1,3-dioxolane)-2,4'-cyclohexane-1', 3"-(5"-ethoxy)-[3H]indol]-2"[1"H]-one is dissolved in 100 ml of dichloromethane, to the solution 3,4 g of sodium borohydride and 0,6 g of benzyltriethylammonium chloride is added. To the mixture at room temperature, in a period of 1 hour, the solution of 29,4 g of trichloroacetic acid in 50 ml of dichloromethane is added. The mixture is stirred for an additional hour, then 130 ml of 1 N sodium hydroxide solution is added to it. After 30 minutes of stirring the ethanol is distilled off in vacuum, the residue is diluted with 100 ml of water and extracted with dichloromethane. The organic phase is evaporated, the oily residue is crystallized from 50 ml of toluene. Thus, 6,25 g of product is obtained, mp.: 123–124° C. Yield: 68%.

Ratio of the isomers (HPLC): cis 98,7%, trans 1%.

What is claimed is:

1. A process for the preparation of spiro[cis-4-(β-hydroxyethyloxy)cyclohexane-[3H]indol]-2'[1'H]-one derivatives of the formula I,

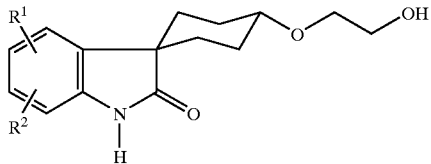

I.

wherein $R^1$ and $R^2$ stand independently from each other for hydrogen, $C_{1-4}$alkyl, $C_{1-4}$alkoxy, $C_{1-4}$alkylthio, $C_{1-4}$polyfluoroalkyl, $C_{1-4}$polyfluoroalkoxy, $C_{3-7}$cycloalkyloxy, $C_{3-7}$cycloalkylthio, phenoxy, benzyloxy or nitro group by reduction of a dispiro [(1,3-dioxolane)-2,4'-cyclohexane-1',3"[3H]indol]-2"-[1"H]-one derivative of the general formula II,

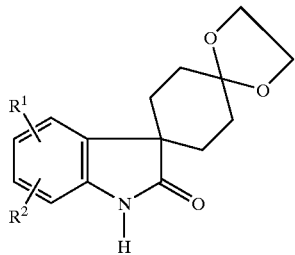

II.

wherein $R^1$ and $R^2$ are as defined above, which comprises carrying out the reduction a.) with sodium cyanoborohydride in the presence of a Lewis acid, or b) with sodium borohydride in the presence of a strong acid.

2. A process according to claim 1, which comprises using as Lewis acid aluminum chloride, zinc chloride, iron/III/chloride or boron trifluoride etherate.

3. A process according to claim 1, which comprises using as strong organic acid trifluoroacetic acid, dichloro acetic acid, methanesulfonic acid, or trifluoromethanesulfonic acid.

4. A process according to claim 1, which comprises using as solvent halogenated hydrocarbons.

5. A process according to claim 2 wherein the Lewis acid is boron trifluoride etherate.

6. A process according to claim 3 wherein the strong acid is trichloroacetic acid.

7. A process according to claim 4 wherein the solvent is dichloromethane.

* * * * *